(12) United States Patent
Yamada et al.

(10) Patent No.: US 9,067,029 B2
(45) Date of Patent: Jun. 30, 2015

(54) AEROSOL ASPIRATOR AND AEROSOL SUCKING METHOD

(75) Inventors: Manabu Yamada, Tokyo (JP); Hiroshi Sasaki, Tokyo (JP); Kazuhiko Katayama, Tokyo (JP); Morio Yajima, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 1359 days.

(21) Appl. No.: 12/363,216

(22) Filed: Jan. 30, 2009

(65) Prior Publication Data

US 2009/0133691 A1 May 28, 2009

Related U.S. Application Data

(63) Continuation of application No. PCT/JP2007/064307, filed on Jul. 20, 2007.

(30) Foreign Application Priority Data

Aug. 1, 2006 (JP) ................................. 2006-209700
Jun. 14, 2007 (JP) ................................. 2007-157501

(51) Int. Cl.
*A61M 11/00* (2006.01)
*A61M 15/00* (2006.01)
(Continued)

(52) U.S. Cl.
CPC ............ *A61M 11/00* (2013.01); *A61M 15/0091* (2013.01); *A61M 11/041* (2013.01);
(Continued)

(58) Field of Classification Search
CPC ........ A62B 9/003; A62B 11/00; A62B 11/30; A62B 11/3001; A61M 16/10; A61M 16/1075; A61M 16/108; A61M 16/1085; A61M 16/109; A61M 16/1095; A61M 16/18; A61M 15/00; A61M 15/0013; A61M 15/0016; A61M 15/0091; A61M 15/0096; A61M 11/00; A61M 11/006; A61M 11/007; A61M 11/008; A61M 11/04; A61M 11/041; A61M 11/042; A61M 2016/10
USPC .............. 128/200.14–200.19, 203.12, 204.17
See application file for complete search history.

(56) References Cited

U.S. PATENT DOCUMENTS 5,277,175 A * 1/1994 Riggs et al. ............... 128/200.21
5,388,574 A * 2/1995 Ingebrethsen ........... 128/203.17
(Continued)

FOREIGN PATENT DOCUMENTS

CN        1205849 A    1/1999
CN        1222089 A    7/1999
(Continued)

*Primary Examiner* — Rachel Young
(74) *Attorney, Agent, or Firm* — Birch, Stewart, Kolasch & Birch, LLP

(57) ABSTRACT

An aerosol aspirator has a casing (2) with a mouthpiece (8) and an outside air inlet (52), a generation passage (56, 60, 68) extending from the outside air inlet (52) to the mouthpiece (8), a syringe pump (18) arranged within the casing (2) to deliver a solution to a distributing position (A) in the generation passage in a fixed amount each time it is activated, and a tubular heater (58) disposed downstream of the distributing position (A) and forming a part of the generation passage. When a user sucks at the mouthpiece (8), the solution at the distributing position (A) is transferred from the position (A) into the heater (58), and within the heater, atomized, and then turns into an aerosol by condensing in sucked air flow, and the aerosol thus formed is sucked by the user with the air flow.

11 Claims, 8 Drawing Sheets

Figure 1:
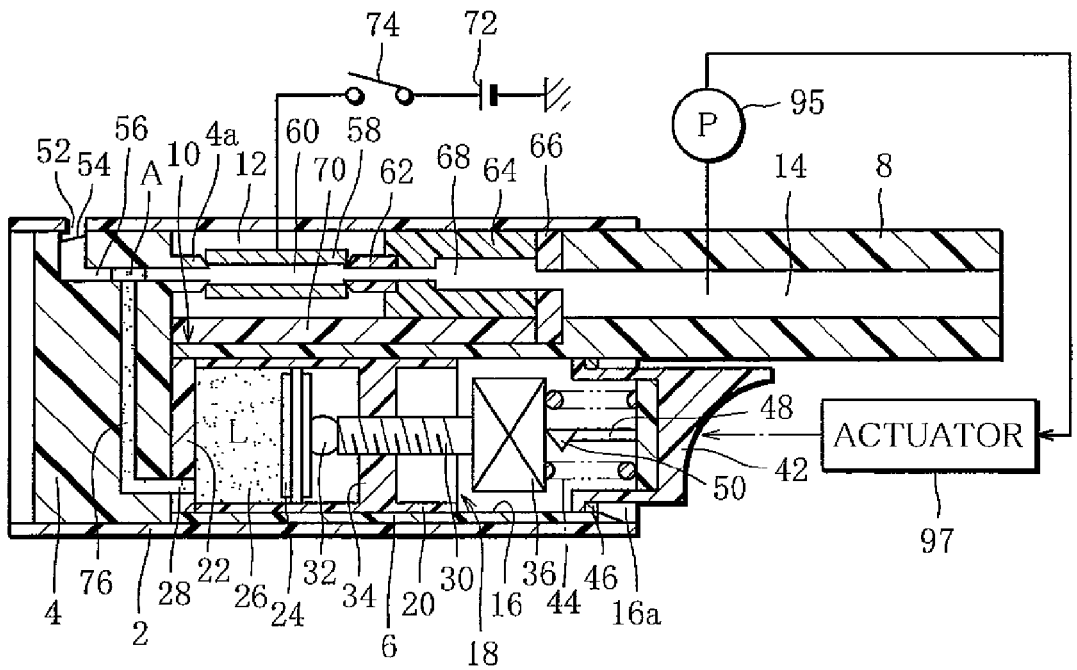

(51) Int. Cl.
*A61M 11/04* (2006.01)
*A61M 16/00* (2006.01)

(52) U.S. Cl.
CPC .......... *A61M 15/00* (2013.01); *A61M 2202/04* (2013.01); *A61M 11/005* (2013.01); *A61M 15/0085* (2013.01); *A61M 2016/0027* (2013.01); *A61M 11/007* (2014.02)

(56) References Cited

U.S. PATENT DOCUMENTS

| | | | |
|---|---|---|---|
| 5,743,251 A | 4/1998 | Howell et al. | |
| 5,894,841 A | 4/1999 | Voges | |
| 6,216,966 B1 | 4/2001 | Prendergast et al. | |
| 6,701,922 B2 * | 3/2004 | Hindle et al. | 128/203.27 |
| 7,954,486 B2 * | 6/2011 | Papania et al. | 128/200.14 |
| 2002/0065685 A1 | 5/2002 | Sasaki et al. | |
| 2002/0079377 A1 | 6/2002 | Nichols | |
| 2003/0145849 A1 | 8/2003 | Drinan et al. | |
| 2003/0223936 A1 | 12/2003 | Balwani et al. | |
| 2004/0050383 A1 * | 3/2004 | Cox et al. | 128/200.14 |
| 2006/0289005 A1 | 12/2006 | Jones et al. | |
| 2007/0125370 A1 * | 6/2007 | Denyer et al. | 128/200.14 |

FOREIGN PATENT DOCUMENTS

| | | |
|---|---|---|
| CN | 1323231 A | 11/2001 |
| JP | 2000-510763 A | 8/2000 |
| JP | 2001-502963 A | 3/2001 |
| JP | 2001-161819 A | 6/2001 |
| JP | 2002-165883 A | 6/2002 |
| JP | 2005-58709 A | 3/2005 |
| JP | 2005-531604 A | 10/2005 |
| JP | 2006-517430 A | 7/2006 |
| WO | WO 97/42993 A2 | 11/1997 |

* cited by examiner

AEROSOL ASPIRATOR AND AEROSOL SUCKING METHOD

This application is a Continuation of copending PCT International Application No. PCT/JP2007/064307 filed on Jul. 20, 2007, which designated the United States and on which priority is claimed under 35 U.S.C. §120. This application also claims priority under 35 U.S.C. §119(a) on Patent Application No(s). 2006-209700 and 2007-157501 filed in Japan on Aug. 1, 2006 and Jun. 14, 2007; respectively, the entire contents of which are hereby incorporated by reference into the present application.

TECHNICAL FIELD

This invention relates to an aerosol aspirator and an aerosol sucking method for providing medicaments, refreshing/relaxing materials or the like to a user in aerosol form.

BACKGROUND ART

An aerosol aspirator of this type is disclosed in Patent Document 1, for example. The aspirator in Patent Document 1 includes a supply device supplying a material in liquid form, a capillary tube with an open end to be filled with the material supplied by the supply device, a mouthpiece arranged adjacent to the open end of the capillary tube, and a heater arranged to surround the open end of the capillary tube. The heater heats, thereby evaporating the material in the capillary tube, so that the material in vapor form spurts out through the open end of the capillary tube.

The user's sucking on the mouthpiece causes contact between the material in vapor form and sucked air, so that the material in vapor form condenses and forms an aerosol, and the aerosol thus formed is drawn into the user's mouth with air.

Patent Document 1: Japanese Patent KOHYO Publication 2000-510763 (WO 97/42993)

DISCLOSURE OF THE INVENTION

Problem to be Solved by the Invention

In the aspirator of Patent Document 1, in order that the user's sucking action can quickly cause aerosol formation, it is required that the heater of the sucking apparatus have been raised to a predetermined temperature in advance. This however causes evaporation of the material in the capillary tube. Thus, in practice, after the user's sucking action is detected, the heater is raised to the predetermined temperature, and after that, a fixed amount of the material is supplied by the supply device to the capillary tube.

Thus, in the aspirator of Patent Document 1, there is a time lag between the user's staring sucking action and the user's actually sucking the aerosol, which time lag causes the user to feel uncomfortable.

Further, when the heating of the material by the heater is stopped, the heater temperature does not drop quickly, so that the material in vapor form continues spurting out through the capillary tube. This prevents the user's sucking a constant amount of aerosol with each sucking action.

An object of the present invention is to provide an aerosol aspirator and method of sucking aerosol which allow the user to suck an aerosol with high responsiveness to the user's sucking action, and which can improve aerosol delivery efficiency and the constancy of the aerosol quantity sucked by the user.

Means for Solving the Problem

In order to achieve the above object, an aerosol aspirator according to the present invention comprises a casing with a mouthpiece, the casing including an outside air inlet open at an outer surface thereof; and a generation device disposed within the casing, for generating an aerosol, the generation device including an aerosol generation passage extending from the outside air inlet to the mouthpiece and having a distributing position and an atomizing surface in a middle part thereof, a supply pump having a solution chamber holding a solution to be turned into an aerosol, for delivering the solution from the solution chamber to the distributing position in a fixed amount each time the supply pump is activated, and an atomizing gadget for atomizing the solution delivered to the distributing position at the atomizing surface.

In this aerosol aspirator, first a fixed amount of a solution is delivered to the distributing position in the aerosol generation passage. When the user's sucking action, namely the user's sucking at the mouthpiece draws air in the aerosol generation passage, the solution that has been delivered to the distributing position is atomized, namely turned into an aerosol at the atomizing surface. The aerosol thus generated is sucked with the air flow by the user through the mouthpiece.

Here, the fixed amount of the solution that has been delivered to the distributing position is atomized simultaneously with or immediately after the user's sucking action. Thus, the aerosol is generated without a time lag relative to the user's sucking action. In other words, the aerosol aspirator of the present invention can generate the aerosol with high responsiveness to the user's sucking action. Further, the solution is delivered to the distributing position in a fixed amount. Thus, the aerosol aspirator of the present invention can generate a fixed amount of aerosol with each sucking action, thereby ensuring the constancy of the aerosol quantity sucked by the user.

Specifically, the aerosol generation passage may be a tubular passage. In this case, the atomizing gadget may include a heater located downstream of the distributing position and upstream of the mouthpiece, the heater having a heating surface serving as the atomizing surface. It is desirable that the heater be tubular in shape and forms a part of the generation passage.

The supply pump may be a syringe pump. In this case, the generation device further includes a liquid passage connecting the syringe pump and the generation passage at the distributing position so that the generation passage is closed with the solution delivered by the syringe pump to the distributing position.

The aspirator may further comprise a switch for activating the heater prior to activating the syringe pump. In this case, the generation device may further include a push button manually operated to activate the syringe pump. Alternatively, the generation device may include an actuator for activating the syringe pump, and a sucking sensing sensor for sensing sucking of air in the generation passage by means of the mouthpiece and activating the actuator.

The distributing position may be defined on the atomizing surface of the atomizing gadget. In this case, the generation device further includes an absorbing member fitted to a discharge port of the supply pump, for temporarily absorbing the solution discharged from the solution chamber, the discharge port being apart from the solution chamber by a predetermined distance, and delivering means for delivering the solution held in the absorbing member to the distributing position on the atomizing surface.

Specifically, the atomizing surface may be formed of a heating surface of a planar heater or a vibrating surface of an ultrasonic vibrator, where the delivering means includes a drive means for advancing and withdrawing the adsorbing member together with the supply pump toward and from the atomizing surface so that the solution is transferred from the absorbing member onto the atomizing surface.

Also in this type of aerosol aspirator, the supply pump may be a syringe pump, and a switch as described above may be provided. As in the first-mentioned type of aerosol aspirator, the generation device may include a manually-operated push button, or alternatively, an actuator for the drive means and a sucking sensing sensor.

When the atomizing gadget includes a heater, the aspirator may further include a control device for controlling operation of the supply pump and the heater such that when air in the generation passage is sucked by means of the mouthpiece, an aerosol obtained by atomizing the solution is produces in the sucked air. Specifically, the control device includes a sucking sensing sensor for sensing the user's sucking action and emitting a sensing signal.

It is desirable that the aerosol aspirator further comprise a power source shared by the supply pump, the heater and the control device, a power switch associated with the power source, and an indicator for indicating the state of at least one of the supply pump, the heater and the power source.

The control device may include a temperature control process in which the heater is activated when the power switch is put in an "ON" position. This temperature control process has a preheating mode of maintaining the heater at a predetermined preheating temperature, and an atomizing heating mode of raising the heater to an atomizing heating temperature higher than the preheating temperature, required to atomize the solution, the atomizing heating mode being initiated when the sensing signal is emitted.

The present invention also provides an aerosol sucking method. The sucking method and further details of the aspirator will become apparent from the description given below with respect to the drawings attached.

BRIEF DESCRIPTION OF THE DRAWINGS

FIG. 1 illustrates a cross-sectional view showing an aerosol aspirator according to a first embodiment.

FIG. 2 illustrates a diagram showing a rotating cam of FIG. 1 in an inactive position, with its development form.

FIG. 3 illustrates a diagram showing the rotating cam of FIG. 2 in an active position.

FIG. 4 illustrates a cross-sectional view showing an aerosol aspirator according to a second embodiment.

FIG. 5 illustrates a cross-sectional view showing an aerosol aspirator according to a third embodiment.

FIG. 6 illustrates a diagram showing a syringe pump on an enlarged scale.

FIG. 7 illustrates a diagram schematically showing the configuration of a control device of FIG. 5 and input/output thereof.

FIG. 8 illustrates a graph showing solution delivery timing and a temperature control process of the heater, performed by the control device of FIG. 5.

FIG. 9 illustrates a diagram for explaining control of current supply to a heater.

FIG. 10 illustrates a diagram for explaining the function of the control unit of FIG. 7 further in detail.

FIG. 11 illustrates a graph showing a variant of the temperature control process and solution delivery timing.

FIG. 12 illustrates a graph showing another variant of the temperature control process and solution supply timing.

BEST MODE OF CARRYING OUT THE INVENTION

FIG. 1 shows an aspirator according to a first embodiment.

The aspirator of FIG. 1 includes a casing 2. The casing 2 has a hollow tubular shape and opens at each end. One open end of the casing 2 is closed with an end wall 4. A cylinder block 6 is fitted within the casing 2. The cylinder block 6 has a bottom at one end thereof, which is in contact with the end wall 4, and an integrally-formed tubular mouthpiece 8 at the other end. The mouthpiece 8 projects outward through the other open end of the casing 2.

The cylinder block 6 has a recess 10 in the outer circumferential surface thereof. The recess 10 extends from the bottom of the cylinder block 6 toward the mouthpiece 8. The recess 10 defines a heater chamber 12, together with the inner circumferential surface of the casing 2. The heater chamber 12 communicates with an internal passage 14 of the mouthpiece 8.

The cylinder block 6 has further a cylinder bore 16. The cylinder bore 16 extends through the cylinder block 6, in the axial direction of the casing 2, parallel to the heater chamber 12. Thus, the cylinder bore 16 has an open end **16*a* on the other side, or mouthpiece 8 side of the cylinder block 6**.

Within the cylinder bore 16, a manually-operated syringe pump 18 is removably accommodated. The syringe pump 18 includes a hollow outer tube 20. The outer tube 20 has a closure wall 22 at one end thereof. The closure wall 22 is in contact with the end wall 4 of the casing 2. A piston 24 is fitted within the outer tube 20. The piston 24 has a piston ring. The piston 24 divides the interior of the outer tube 20 into two chambers, of which one is a pump chamber 26 defined between one end face of the piston 24 and the closure wall 22, and the other is a rod chamber. The pump chamber 26 communicates with a discharge port 28. The discharge port 28 is formed in the closure wall 22.

The pump chamber 26 is used as a solution chamber, and charged with a solution L in advance. The solution L is a medicament, a refreshing/relaxing material or the like which is to be turned into an aerosol. When the solution L is a refreshing/relaxing material, it can contain constituents of tobacco, for example.

Within the rod chamber of the outer tube 20, a screw rod 30 is arranged. The screw red 30 is connected to the piston 24 by a ball joint 32 at one end thereof, and extends coaxially with the outer tube 20. The rod chamber of the outer tube 20 is divided by a partition wall 34. The partition wall 34 has a threaded hole coaxial with the outer tube 20. The threaded hole extends through the partition wall 34. Thus, the screw rod 30 extends through the partition wall 34, meshing with the threaded hole. Incidentally, the partition wall 34 is formed integrally with the outer tube 20.

The screw rod 30 has an end projecting beyond the other end of the outer tube 20, and this projecting end is connected with a rotating cam 36. The rotating cam 36 is arranged within the cylinder bore 16, and can rotate integrally with the screw rod 30, allowing axial movement of the screw rod 30. Specifically, the rotating cam 36 and the screw rod 30 are spline-connected.

As shown in FIG. 2, the rotating cam 36 has two rows of teeth on its circumferential surface, where the teeth in each rows are distributed all over the circumference of the rotating cam 36 and the two tooth rows are apart from each other in the axial direction of the rotating cam 36. One of the two tooth row includes cam teeth 38, while the other includes cam teeth 40. The pitch between the adjacent two cam teeth 38 is equal to the pitch between the adjacent two cam teeth 40. As clear from FIG. 2, however, the position of each cam tooth 38 is half the pitch displaced from the position of each cam tooth 40 in the circumferential direction of the rotating cam 36.

Each cam tooth 38 is triangular in shape with two sides projecting toward the cam tooth 40. One of these two sides, specifically an upper one of the two sides viewed in FIG. 2 forms a cam face 38a. The cam face 38a is inclined relative to the axial direction of the rotating cam 36. Each cam tooth 40 is also triangular in shape with two sides projecting toward the cam tooth 38. One of these two sides of the cam tooth 40 forms a cam face 40b. The cam face 40b is inclined relative to the axial direction of the rotating cam 36, oppositely to the cam face 38a to be at right angles to the cam face 38a.

The cam faces 38a and 40b are displaced from each other in the radial direction of the rotating cam 36. More specifically, the cam face 38a is located at the radially outer side of the cam face 40a.

A proximal end of a push button 42 is slidably fitted in the open end 16a of the cylinder bore 16. The push button 42 extends from the cylinder bore 16 outward, beneath the mouthpiece 8. A return spring 44 is arranged between the push button 42 and the rotating cam 44. The return spring 44 is a compression coil spring. The return spring 44 exerts on the push button 42 such force that tends to cause the push button 42 to project through the open end 16a outward, so that the proximal end of the push button 42 is pressed against a stopper ring 46. The stopper ring 46 is fixed at the open end 16a.

The push button 42 has a push rod 48. The push rod 48 extends from the push button 42 toward the rotating cam 36. A pusher 50 is attached to the distal end of the push rod 48. The pusher 50 is triangular in shape with two pusher faces 50a, 50b. The pusher faces 50a, 50bare inclined oppositely relative to the axial direction of the rotating cam 36, and able to engage the cam face 38a of the cam tooth 38 and the cam face 40b of the cam tooth 40, respectively.

Figure 2:
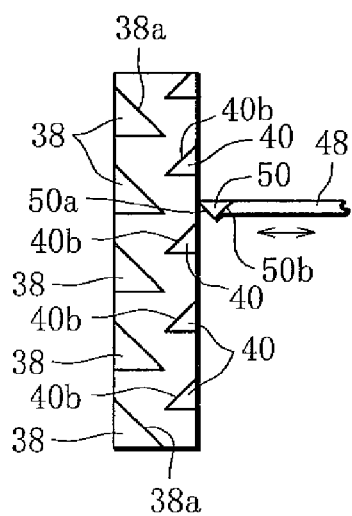
Figure 3:
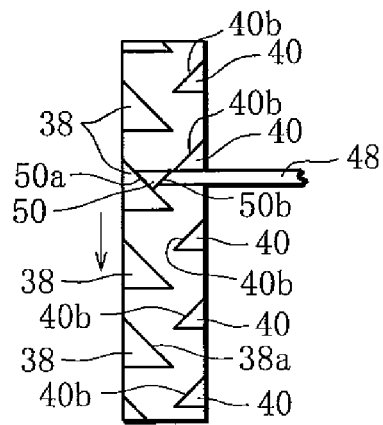

More specifically, when the push button 42 is depressed from a rest position shown in FIG. 1 further into the cylinder bore 16 against the force exerted by the return spring 44, the pusher 50 of the pusher rod 48 moves from the position shown in FIG. 2, passing between two adjacent cam teeth 40, so that the pusher face 50a comes into contact with the cam face 38a of a cam tooth 38 as shown in FIG. 3 and pushes the rotating cam 36 to the left side in FIG. 3. At this time, since the pusher face 50a and the cam face 38a are both inclined relative to the axial direction of the rotating cam 16, the pusher 50's pushing force produces a component thereof which tends to cause the rotating cam 36 to rotate in one direction. Consequently, the rotating cam 36 rotates about the axis thereof in one direction by a predetermined angle.

Then, when the push button 42 is released, the push button 42 with the push rod 48 returns to the rest position by the force exerted by the return spring 44, so that the pusher face 50b of the pusher 50 comes into contact with the cam face 40b of a posterior one 40 of the aforementioned two cam teeth 40 viewed in the direction of rotation of the rotating cam 36 and pushes this cam face 40b, thereby causing the rotating cam 36 to further rotate about the axis in the same direction by a predetermined angle. The push rod 48 then returns to the position shown in FIG. 2.

As clear from the above description, each time the push button 42 is depressed and released, the rotating cam 36 is rotated in the same direction by a predetermined angle. Since the rotating cam 36 is connected with the screw rod 30, the screw rod 30 intermittently rotates with the rotating cam 36. Since the screw rod 30 meshes with the threaded hole in the dividing wall 34, the screw rod 30 advances a predetermined distance toward the piston 24, thereby forcing the piston 24 into the pump chamber 26, each time the screw rod 30 rotates. Consequently, the solution L in the pump chamber 26 is discharged through the discharge port 28 of the syringe pump 18 in a fixed amount each time.

The casing 2 has an outside air inlet 52 open at its outer surface. The outside air inlet 52 is located near the one end of the casing 2. The outside air inlet 52 is connected to the internal passage of the mouthpiece 8 by an aerosol generation passage. Next, this generation passage will be described in detail.

The generation passage includes an introduction passage 56 formed in the end wall 4 of the casing 2. The introduction passage 56 has an L shape and extends from the outside air inlet 52 to the heater chamber 12. As necessary, a check valve 54 is inserted in the introduction passage 54. In the present embodiment, the check valve 54 is a reed valve located near the outside air inlet 52, which allows only flow of outside air from the outside air inlet 52 into the introduction passage 56 and blocks air's flowing out of the introduction passage 56 through the outside air inlet 52.

A tubular heater 58 is located within the heater chamber 12. The heater 58 has an internal heating passage 60. The heating passage 60 is connected to the introduction passage 56 at one end thereof. Between the heater 58 and the mouthpiece 8, a joint 62, a connection pipe 64 and a connection ring 66 are disposed in this order, as viewed from the heater 58 side. These elements 62 to 66 define a connection passage 68 therein which connects the heating passage 60 and the internal passage 14 of the mouthpiece 14. As clear from FIG. 1, the heating passage 60, the connection passage 68 and the internal passage 14 are linearly arranged.

More specifically, the connection pipe 64 is placed on a spacer 70 which is located at the bottom of the heater chamber 12. The end wall 4 has a joint 4a integrally formed on its inner face and similar in shape to the joint 62. The joints 4a and 62 each have a taper end tapering toward the heater 58, and the heater 58 is held between the taper ends of the joints 4a, 62 to be not in contact with the spacer 70. Thus, within the heater chamber 12, an annular space surrounding the heater 58 is provided. The introduction passage 56 extends though the joint 4a to communicate with the heating passage 60. The joint 4a may be a separate member from the end wall 4.

The heater 58 is electrically connected to a power source 72 with a switch 74 between. The power source 72 is accommodated within the casing 2, while the switch 74 is mounted on the outer surface of the casing 2. Although the heater 58 should desirably be a ceramic heater, it may be made of another chemical- and heat-resistant conductive material such as stainless steel.

From the generation passage, specifically from the introduction passage 56 extends a liquid passage 76. The liquid passage 76 is formed in the end wall 4 of the casing 2 and connected to the discharge port 28 of the syringe pump 18.

Before the above-described aerosol aspirator is used first time, the solution L in the pump chamber 26 is delivered into the liquid passage 76 in a predetermined amount, so that the liquid passage 76 is filled with the solution L.

In this state, when the user puts the switch 74 in an "ON" position, the power source 72 supplies power to the heater 58, so that the heater 58 rises to a predetermined temperature. As long as the switch 74 is kept in the "ON" position, the heater 58 is maintained at the predetermined heating temperature.

In this state, when the user depresses the push button 42 and then releases it, the syringe pump 18 operates as described above, so that the solution L in the pump chamber 26 of the syringe pump 18 is delivered to the generation passage, specifically the introduction passage 56, via the liquid passage 76, in a fixed amount.

More specifically, the position at which the liquid passage 76 is connected to the introduction passage 56 defines a solution L distributing position A. The syringe pump 18 delivers the solution L from the pump chamber 26 to the distributing position A in a fixed amount each time it is activated, and the solution L that has reached the distributing position A plugs the introduction passage 56 at the distributing position A.

Then, when the user sucks on the mouthpiece 8 to draw air in the generation passage to the mouthpiece, air downstream of the distributing position A within the generation passage flows toward the mouthpiece 8, since the generation passage is closed at the distributing position. With this air flow, the solution L at the distributing position A instantaneously moves from the distributing position A toward the heater 58, so that all the delivered solution enters the heating passage 60 of the heater 58, and outside air is drawn into the generation passage, specifically the introduction passage 56 through the outside air inlet 52.

Since the heater 58 has been raised to the predetermined temperature as mentioned above, the solution L that has entered the heating passage 60 receives heat from the inner surface of the heater 58 and evaporates quickly. Upon contacting the air flow mentioned above, the vapor resulting from the solution L quickly condenses and forms an aerosol. The aerosol formed is drawn into the user's mouth, through the internal passage 14 of the mouthpiece 8, with the air flow.

Thus, the user can draw the aerosol formed from the solution L into the mouth simultaneously with his/her sucking on the mouthpiece 8. The amount of the aerosol generated is determined by the amount of the solution L delivered to the distributing position A, which means that a constant amount of aerosol is generated with each sucking action of the user. Thus, this aerosol aspirator can generate an aerosol with high responsiveness to the user's sucking action and can ensure the constancy of aerosol generation quantity.

In the aspirator according to the first embodiment, the push button 42 and the rotating cam 36 may be replaced with a linear or rotating actuator 97. The actuator 97 rotates the screw rod 30 of the syringe pump 18 in one direction by a predetermined angle at a time, thereby causing the solution L to be delivered from the syringe pump 18 to the distributing position A in a fixed amount.

The aspirator according to the first embodiment can be adapted such that the actuator 97 is activated in association with the user's sucking action. In this case, as shown in FIG. 1, the aspirator has a sucking sensing sensor 95 in the generation passage or the internal passage 14 of the mouthpiece 8. When the user sucks on the mouthpiece 8, the sucking sensing sensor 8 detects a pressure drop in the generation passage or the internal passage 14, and supplies a detection signal to the actuator 97r thereby activating the actuator 97.

When the delivery of the solution L to the distributing position A is caused in association with the user's sucking action, the delivery of the solution L is completed in an early stage of the user's sucking action. This ensures that an aerosol is generated with sufficiently high responsiveness to the sucking action not to cause the user to feel uncomfortable.

In the aspirator according to the first embodiment, the push button 42 may be replaced with a linear actuator for rotating the rotating cam 36, and the heater 58 may be replaced with a planar heater. When the planar heater is used, the heater chamber 12 forms a part of the generation passage. Further, the aspirator according to the first embodiment may include a valve at the downstream end of the liquid passage 76, where the valve is opened in association with activating the syringe pump 18.

Figure 4:
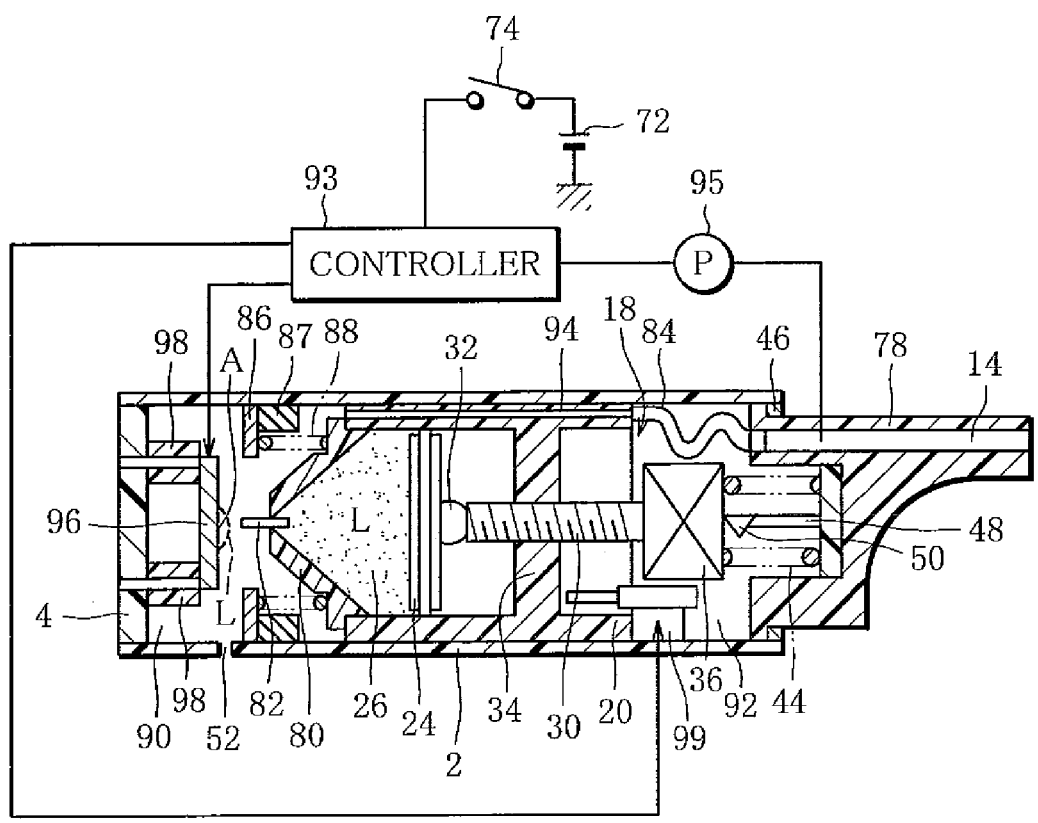

FIG. 4 shows an aerosol aspirator according to a second embodiment.

In the description of the second embodiment below, members and parts having the same function as those of the first embodiment are assigned the same reference characters, and the explanation of such parts and members are omitted.

The aerosol aspirator according to the second embodiment has a push-button mouthpiece 78 at an open end of the casing 2. This mouthpiece 78 functions as both the mouthpiece 8 and the push button 4 of the first embodiment. The proximal end of the mouthpiece 78 is slidably fitted into the open end of the casing 2.

A syringe pump 18 has a closure wall 80, which substitutes the closure wall 22 of the first embodiment. The closure wall 80 is in the shape of a truncated cone projecting toward the end wall 4 of the casing 2, and has a discharge port 28 at the tip end. A porous plug 82 is fitted in the discharge port 28. The plug 82 is made of a flexible sponge and projects from the closure wall 80 toward the end wall 4.

In the second embodiment, an outer cylinder 20 of the syringe pump 18 is fitted within the casing 2 and can reciprocate a predetermined distance in the axial direction of the casing 2. More specifically, an annular spring seat 86 is mounted to the inner circumferential surface of the casing 2. The spring seat 86 is located near the closure wall 80 of the outer cylinder 20. A compression coil spring, or return spring 88 is arranged between the spring seat 86 and the closure wall 80. The return spring 88 presses the outer cylinder 20 toward the mouthpiece 78. Here, the compression spring 88 is sufficiently stronger than the return spring 44 for the mouthpiece 78. The spring seat 86 has an end face facing the closure wall 80. An annular stopper 87 is attached to this end face of the spring seat 86. The stopper 87 restricts the movement of the syringe pump 18 toward the end wall 4 of the casing 2.

The syringe pump 18 divides the interior of the casing 2 into an atomizing chamber 90 adjacent to the end wall 4 and a cam chamber 92 adjacent to the mouthpiece 78. The rotating cam 36 as described above is arranged within the cam chamber 92. An axial passage 94 is formed in the circumferential wall of the outer cylinder 20. The axial passage 94 extends through the wall of the outer cylinder 20 to connect the atomizing chamber 90 and the cam chamber 92. A flexible tube 84 is arranged within the cam chamber 92. The tube 84 connects the axial passage 94 and the internal passage 14 of the mouthpiece 78. The tube 84 has a length enough to allow advancement and withdrawal of the mouthpiece 78 relative to the syringe pump 18 and reciprocation of the syringe pump 18, while maintaining the connection between the axial passage 94 and the internal passage 14. An outside air inlet 52 communicates with the atomizing chamber 90. Thus, in the second embodiment, the atomizing chamber 90, the axial passage 94 and the tube 84 forms an aerosol generation passage.

An atomizing plate 96 is located within the atomizing chamber 90. The atomizing plate 90 is mounted to the end wall 4 of the casing 2 by a plurality of supports 98. The atomizing plate 96 has a flat atomizing surface facing the closure wall 80 of the syringe pump 18. A distributing position A is defined on this atomizing surface.

Specifically, the atomizing plate 96 is formed of a planar heater or an ultrasonic vibrator, and the atomizing surface is a heating surface of the heater or a vibrating surface of the ultrasonic vibrator.

For the sake of simplicity, the description will be given on the assumption that the atomizing plate 96 is a heater plate.

When the syringe pump 18 is in a rest position shown in FIG. 4, the plug 82 is apart by a predetermined distance from the heater plate 96. This distance is slightly shorter than the distance that the syringe pump 18 moves from the rest position until it hits against the stopper 87.

The heater plate 96 is electrically connected to a controller 93. The controller 93 is connected to the power source 72 with the switch 74 between, and to the sucking sensing sensor 95. The controller 93, the power source 72 and the sucking sensing sensor 95 are accommodated within the casing 2.

As shown in FIG. 4, a linear actuator 99 is arranged within the cam chamber 92. The liner actuator 99 is electrically connected to the controller 93. By receiving a command from the controller 93, the linear actuator 99 is activated to move the syringe pump 18 from the rest position shown in the drawing toward the heater plate 96.

In this aerosol aspirator according to the second embodiment, when the user puts the switch 74 in an "ON" position, the controller 93 supplies power to the heater plate 96, thereby raising the heater plate 96 to a predetermined temperature.

Then, when the user depresses the mouthpiece 78 into the casing 2 and then releases it, the push rod 48 and the rotating cam 36 work together in the same way as in the first embodiment to cause a fixed amount of the solution L to be discharged from the syringe pump 18 through the discharge port 28. The solution L discharged is absorbed by the plug 82 and held within the plug 82.

As mentioned above, the return spring 44 on the mouthpiece 78 is weaker than the return spring 88. Thus, even when the mouthpiece 78 is depressed into the casing 2, the syringe pump 18 stays in the rest position shown in the drawing.

Then, when the user sucks on the mouthpiece 78 and this sucking action is detected by the sucking sensing sensor 95, the sucking sensing sensor 95 supplies a detection signal to the controller 93. Upon this, the controller 93 activates the linear actuator 99. Consequently, the linear actuator 99 forces the syringe pump 18 forward through the partition wall 34, against the force exerted by the return spring 88, from the rest position toward the heater plate 96. During this movement of the syringe pump 18, the plug 82 butts the heater plate 96 before the syringe pump 18 hits against the stopper 87. Such butting causes compression of the plug 82, so that the solution L held by the plug 82 is squeezed out of the plug 82 onto the heater plate 96 (see a two-dot chain line in FIG. 4). In other words, the solution L in the fixed amount is transferred onto the heater plate 96 or the distributing position A.

Then, when the syringe pump 18 hits against the stopper 87 or the linear actuator 99 finishes a predetermined stroke, the controller 93 deactivates the linear actuator 99. Consequently, the syringe pump 18 is returned to the rest position shown in FIG. 4 by the force exerted by the return spring 88, so that the plug 82 separates from the heater plate 96.

As described above, the return spring 88, the controller 93 and the linear actuator 99 work together to distribute the solution L from the pump chamber 26 of the syringe pump 18 to the distributing position A in a fixed amount in each stroke.

Before the solution L is distributed to the position A, the heater plate has been raised to the predetermine temperature. Thus, when the solution L is distributed onto the heater plate 96, the solution evaporates quickly. Then, upon contacting the air flow in the atomizing chamber 90, the vapor resulting from the solution L is atomized, namely turns into an aerosol. Thus, the user can suck a fixed amount of aerosol together with air immediately after starting the sucking action. In other words, also the aerosol aspirator according to the second embodiment ensures the constancy of aerosol sucking quantity and high responsiveness.

It is to be noted that even if the heater plate 96 is always at the predetermined raised temperature, the plug 82 stays away from the heater plate by the predetermined distance 96 unless the user does the sucking action, so that the solution L held within the plug 92 is prevented from evaporating by receiving heat from the heater plate 96. This contributes much to the constancy of aerosol generation quantity.

When the aerosol aspirator according to the second embodiment uses, as the atomizing plate, an ultrasonic vibrating plate 96 in place of the heater plate, the ultrasonic vibrating plate 96 can turn the solution L into an aerosol directly, namely without evaporating it. Such ultrasonic vibrating plate 96 is particularly suited for turning into an aerosol a solution that varies in qualities under rapid heating.

FIG. 5 shows an aerosol aspirator according to a third embodiment.

The aerosol aspirator of FIG. 5 includes a casing 102 made of synthetic resin. The casing 102 comprises, for example three casing parts, i.e., an upper casing part **102*a*, an intermediate casing part 102*b* and a lower casing part 102*c***.

A hollow mouthpiece 104 extends through a rear wall of the upper casing part **102*a* backward, namely to the right side in FIG. 5. This mouthpiece 104 is detachably attached to the upper casing part 102*b*. Specifically, a support ring 106 is arranged within the upper casing part 102*a* to be located adjacent to the rear wall. The mouthpiece 104 extends through the rear wall of the upper casing part 102*a*, with its inner end removably fitted into the support ring 106**.

The upper casing part **2*a* has an outside air inlet 111 open at the upper surface, near the front end thereof. The outside air inlet 111 is connected to the inner end of the mouthpiece 104 by an aerosol generation passage 110. The aerosol generation passage 110 extends within the upper casing part 102*a*. More specifically, in the third embodiment, a T-tube 112, a heater holder 114, a heater 116 and a heater holder 118, disposed in this order from the left side in FIG. 5, form the generation passage 110. The heater holder 114, the heater 116 and the heater holder 118 are tubular in shape and disposed coaxially with the mouthpiece 104. The heater holders 114, 118** have heat-resistant property.

The T-tube 112 has first and second ends coaxial with the mouthpiece 104 and a third end connected to the outside air inlet 111. The first end of the T-tube 112 is connected to the heater holder 116, and the second end of the T-tube 112 is closed. The internal passages of the heater holder 114, the heater 116 and the heater holder 118 are approximately equal in cross-sectional area to the internal passage of the mouthpiece 104. A reed-valve type check valve (not shown) may be provided at the outside air inlet 111 to allow only an air flow from the outside air inlet 111 into the generation passage 110.

The heater holders 114, 118 hold the heater 116 in a manner pinching the heater 116 between them. The heater holder 114 is arranged within the upper casing part 102 by means of the support ring 120, while the heater holder 118 is inserted in the aforementioned support ring 106, thereby connected to the mouthpiece 104.

Although in the third embodiment now being discussed, the heater 116 is a ceramic heater, it may be made of another chemical- and heat-resistant conductive material such as stainless steel.

Preferably, the upper casing part 102a should include a lid (not shown) that can be opened and closed to allow the heater 116 to be removed from the upper casing part 102a.

The intermediate casing part 102b defines a rear chamber 122 and a front chamber 124 therein, where the rear chamber 122 and the front chamber 124 are separated by a partition wall. The rear chamber 122 extends between the aforementioned support rings 120 and 106.

Within the rear chamber 122, a support block 126 is arranged, and a syringe holder 128 is mounted on the support block 126. The syringe holder 128 is rectangular in cross section and extends parallel to the aforementioned generation passage 110. The syringe holder 128 has a stepped cylinder bore defined therein. The cylinder bore is open at each end of the syringe holder 128.

A cartridge type syringe pump 130 is removably inserted in the syringe holder 128. A stopper sleeve 128a is fitted within the syringe holder 128, at its front end thereof as viewed in the direction of inserting the syringe pump 130. Thus, when the syringe pump 130 is inserted in the syringe holder 128, the syringe pump 130 butts the stopper sleeve 28a.

Figure 6:
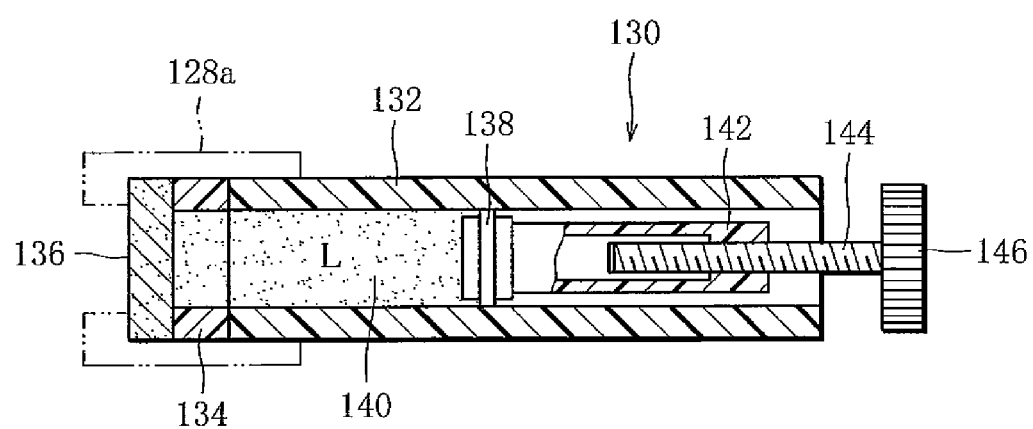

FIG. 6 shows the syringe pump 130 in detail.

The syringe pump 130 includes an outer cylinder 132. A circular septum 136 is mounted on the front end of the cylinder 132 by means of an annular holder 134. A piston 138 is fitted into the cylinder 132. The piston 138 is allowed to slide in the cylinder 132 but prevented from rotating about the axis thereof.

A pump chamber 140 is defined in the cylinder 132, between the piston 138 and the septum 136. The pump chamber 140 is filled with a solution L of a type mentioned above. The piston 138 has a hollow drive rack 142. The drive rack 142 extends from the piston 138 toward the rear end of the outer cylinder 132, coaxially with the piston 138. The drive rack 142 has an end wall at the rear end thereof. The end wall is formed as a nut, or in other words, the end wall of the drive rack 142 has a threaded hole, through which a screw rod 144 is screwed into the drive rack 142. The screw rod 144 meshes with the threaded hole, with a front end located within the drive rack 142 and a rear end outside the drive rack 142.

Figure 5:
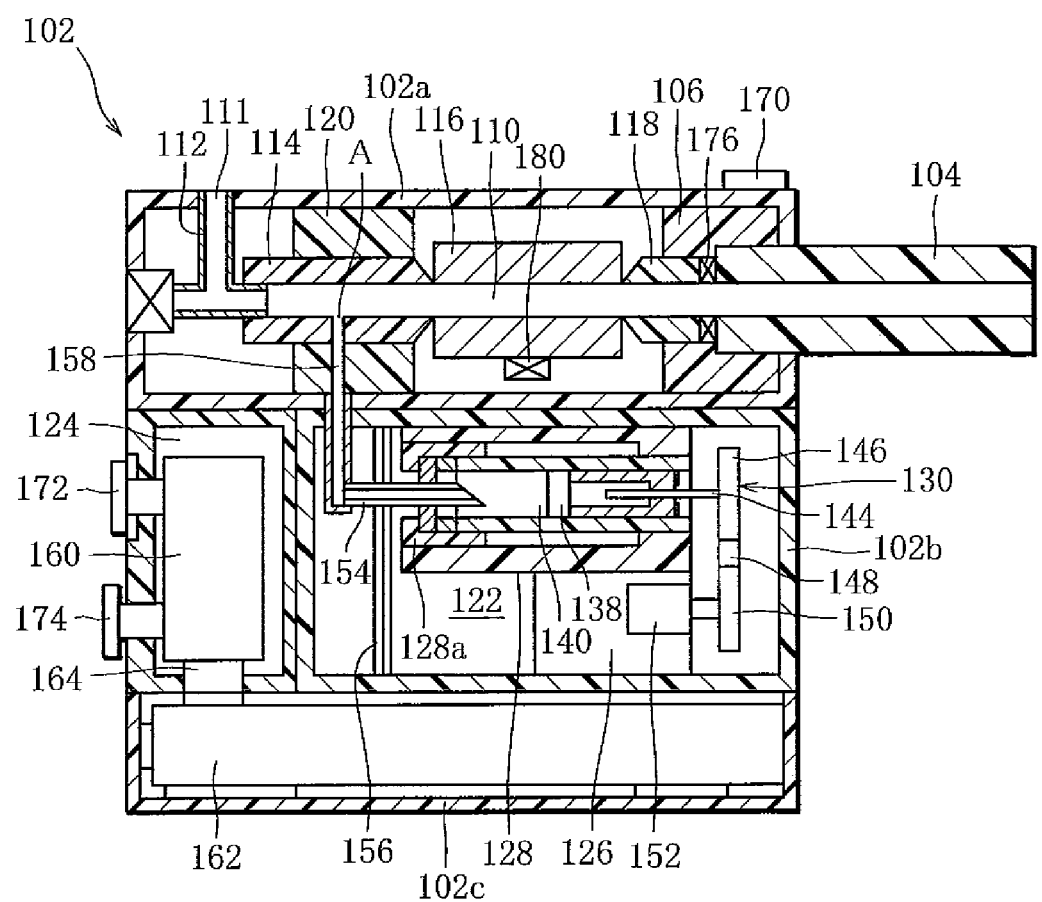

A gear 146 is mounted on the rear end of the screw rod 144. As shown in FIG. 5, when the syringe pump 130 is set within the syringe holder 128, the gear 146 meshes with a reduction gear 148 meshing with a drive gear 150. The drive gear 150 is connected to a motor 152 as a drive source. The motor 152 can rotate normally and reversely and is mounted on the aforementioned support block 126. The motor 142 may be any of a step motor, a direct-current motor and a servomotor. The reduction gear 148 is rotatably supported within the rear chamber 122.

As clear from FIG. 5, when the syringe pump 130 is set within the syringe holder 128, a hollow needle 154 is inserted into the pump chamber 140 of the syringe pump 130, through the septum 136. The needle 154 is supported by a disc-shaped needle holder 156. The needle holder 156 is located within the rear chamber 122.

The needle 154 is connected to a liquid passage 158, and the liquid passage 158 is connected to the aforementioned generation passage 110.

More specifically, the liquid passage 158 includes an internal passage extending in the heater holder 114, the support ring 120 and the upper and intermediate casing parts 102a, 102b, and a connection pipe extending within the rear chamber to connect the internal passage and the needle 154. The internal passage has an open end at a distributing position A defined on the inner surface of the heater holder 14.

Desirably, a lid (not shown) allowed to be opened and closed is provided at the back wall of the intermediate casing part 102b. With the lid opened, insertion of the syringe pump 130 into the syringe holder 128 and removal of the syringe pump 130 from the syringe holder 128 are possible.

A control device 160 is accommodated in the front chamber 124, and an electric cell 162 is accommodated in the aforementioned lower casing part 102c. For the electrical cell 162, a primary cell such as a fuel cell or a nickel-hydrogen cell, or a secondary cell such as a nickel-cadmium cell, a nickel-hydrogen cell or a lithium cell can be used. Tn the embodiment now being discussed, the electrical cell 162 is a lithium cell. The lower casing part 102c has an openable and closable lid (not shown), and with the lid opened, the cell 162 can be replaced.

By being set in the lower casing part 102c, the electrical cell 162 becomes electrically connected to the control device 160 via a connector 164, to serves as a power source for not only the control device 160 but also the aforementioned heater 116 and motor 152.

Figure 7:
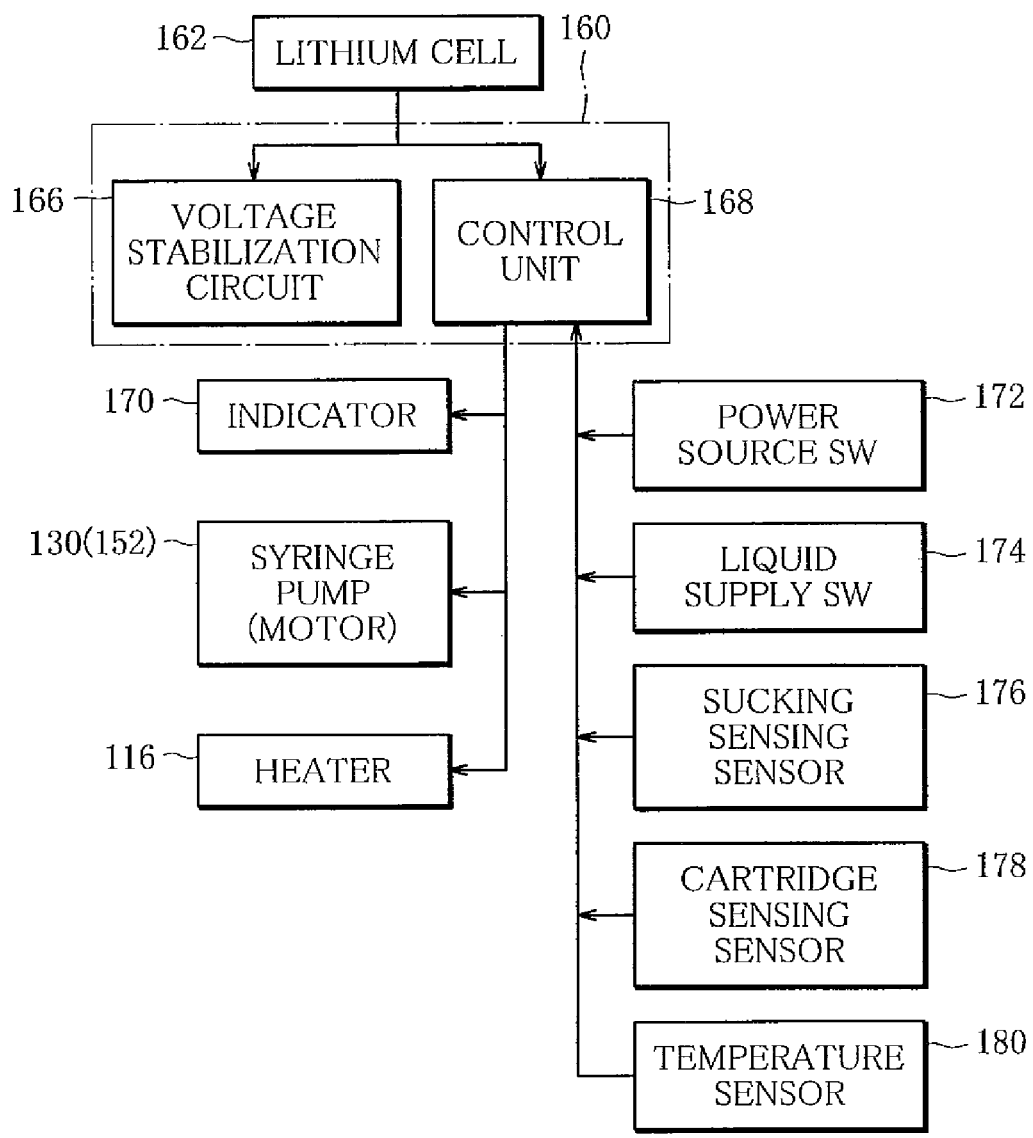

As shown in FIG. 7, the control device 160 includes a voltage stabilization circuit 166 and a control unit 168, and the control unit 168 includes a microprocessor, memory, a peripheral, an input-output interface, etc., for example.

To the output of the control unit 168, the aforementioned heater 116, the motor 152 for the syringe pump 130, and an indicator 170 are electrically connected. The indicator 170 is, for example attached to the upper surface of the upper casing part 102a, near the mouthpiece 104.

To the input of the control unit 168, a power source switch 172 manually operated to allow or shut off the supply of power from the electrical cell 162, a liquid supply switch 174 to allow manual operation of the syringe pump 130, a sucking sensing sensor 176 to sense the user's sucking on the mouthpiece 104 that draws air in the generation passage to the mouthpiece, a cartridge sensing sensor 178 to sense insertion of the syringe pump 130 in the syringe holder 128, a temperature sensor 180 to detect temperature of the heater 116, etc. are electrically connected.

The power source switch 172 and the liquid supply switch 174 are disposed at the front wall as shown in FIG. 5, or a side wall. In the embodiment now being discussed, the sucking sensing sensor 176 is a pressure sensor disposed between the aforementioned heater holder 118 and the mouthpiece 104 to detect pressure in the generation passage 110.

As the sucking sensing sensor 176, a flow sensor to detect air flow in the generation passage 110 may be used in place of the pressure sensor. In this case, the aforementioned T-tube 112 has the second end open at the outer surface of the upper casing part 102a, and the flow sensor is disposed at this open second end.

The cartridge sensing sensor 178 is, for example a limit switch and disposed on the stopper sleeve 128a of the syringe holder 128. The cartridge sensing sensor 178 is activated by the syringe pump 130 that has been inserted in the syringe holder 128. The temperature sensor 180 is attached to the heater 116. A thermistor, a thermocouple or a platinum resistance wire can be used as the temperature sensor 180.

Alternatively, the control unit 168 may function as the temperature sensor 180. Specifically, the control unit 168 may estimate the temperature of the heater 116 from the power supplied to the heater 116.

The control unit 168 receives signals from the switches and sensors connected to its input, and controls heating of the heater 116 and operation of the syringe pump 130 on the basis of those signals. The control unit 168 further detects the operating state of at least one of the heater 116, the syringe pump 130 and the cell 162, and causes the indicator 170 to present the detection result. The indicator 170 will be described later.

Prior to describing the aerosol sucking method using the aspirator according to the third embodiment, preprocessing performed subsequent to insertion of the syringe pump 130 into the syringe holder 128, and postprocessing performed prior to replacement of the syringe pump 130 will be described.

When a syringe pump 130 is inserted in the syringe holder 128 for the first time or a new syringe pump 130 is inserted in the syringe holder 128 to replace the old one 130, the aforementioned cartridge sensing sensor 178 senses the insertion of the syringe pump 130 and supplies a sensing signal to the control unit 178, thereby causing the control unit 167 to perform preprocessing.

Specifically, the control unit 168 drives the motor 152 for the syringe pump 130 to rotate in one direction, thereby causing the gear 146 to rotate by a predetermined angle. Consequently, the piston 138 of the syringe pump 130 advances a predetermined distance in the direction causing a reduction in volume of the pump chamber 140, namely toward the septum 138, thereby discharging the solution L from the pump chamber 140 of the syringe pump 130 into the liquid passage 158. The amount of the solution L discharged at this time corresponds to the volume of the liquid passage 158, so that the liquid passage 15 is filled with the solution L. With this, the preprocessing is completed.

When the solution L in the syringe pump 130 decreases to a predetermined amount or below so that the syringe pump 130 requires replacement, the control unit 168 drives the motor 152 for the syringe pump 130 to rotate in the reverse direction, thereby causing the piston to withdraw. Such withdrawal of the piston 138 creates a negative pressure in the pump chamber 140. Consequently, the aforementioned solution L filling the liquid passage 158 is all drawn back into the pump chamber 140, with which the postprocessing is completed.

As a result of the above-described postprocessing, the liquid passage 158 becomes empty. Thus, if the syringe pump 130 is replaced with a new syringe pump holding a solution different from the solution L, mixing of the different solutions does not occur in the liquid passage 158.

Next, the basic operation of the aspirator according to the third embodiment, or the basic aerosol sucking method will be described.

Prior to sucking on the mouthpiece 104, the user first puts the liquid supply switch 174 in an "ON" position. Upon receiving an "ON" signal from the liquid supply switch 174, the control unit 168 causes the piston 138 of the syringe pump 130 to advance a predetermined distance. Consequently, a fixed amount of the solution L is delivered from the pump chamber 140 of the syringe pump 130 to the distributing position A in the generation passage 110, and the solution L delivered plugs the generation passage 110 at the distributing position A.

Then, when the user sucks on the mouthpiece 104, air in the generation passage 110 is drawn to the mouthpiece 104, and the solution L is transferred from the distributing position A into the heater 116, following the air drawn in. If, at this time, the heater 116 has reached the atomizing heating temperature, i.e., the temperature enough to heat and atomize the solution L, all the solution L transferred into the heater 116 turns into an aerosol at once, and the aerosol thus formed is drawn into the user's mouth with the air flow.

Figure 8:
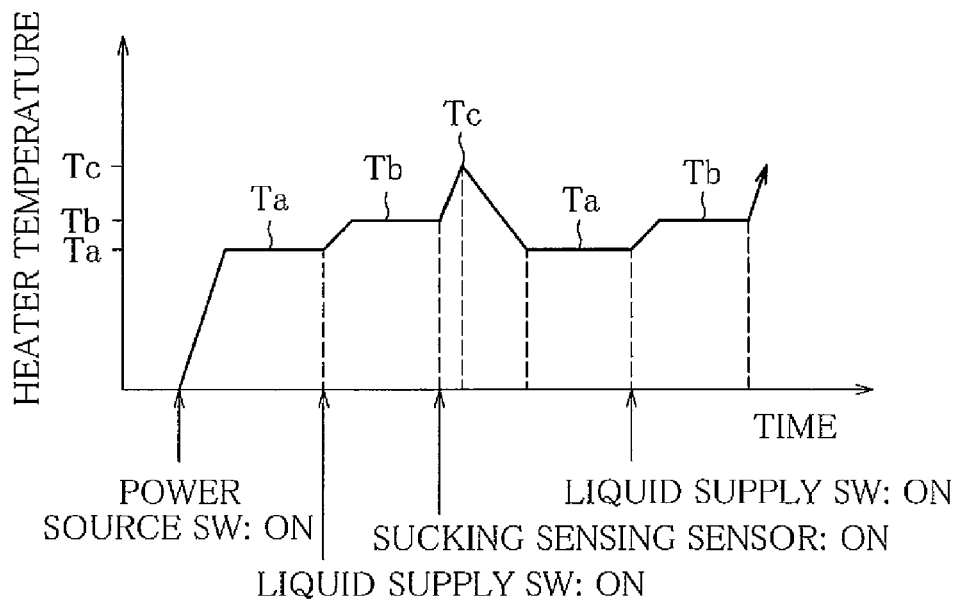

The control unit 168 can control the temperature of the heater 116, for example in a temperature control process shown in FIG. 8. Next, this temperature control process will be described.

Upon the user's putting the power switch 172 in the "ON" position, the control unit 168 starts supply of power to the heater 16. While monitoring the heater 116 temperature on the basis of a detection signal from the temperature sensor 180, the control unit 168 quickly raises the heater 116 to a predetermined early preheating temperature Ta (150° C., for example) and maintains the heater at this early preheating temperature Ta (first stage of a preheating mode).

Then, when the user puts the liquid supply switch 174 in the "ON" position with the intention to suck an aerosol and an "ON" signal is supplied from the liquid supply switch 174 to the control unit 168, the control unit 168 drives the motor 152 for the syringe pump 130, thereby causing the piston 138 of the syringe pump 130 to advance a predetermined distance. Consequently, a fixed amount of the solution L is delivered to the distributing position A in the generation passage 110 from the pump chamber 140 of the syringe pump 130 via the liquid passage 158, and as mentioned above, the solution L delivered closes the generation passage 110 at the distributing position A.

At the same time as the solution L is delivered, the control unit 168 raises the heater 116 to a late preheating temperature Tb (185° C., for example) higher than the early preheating temperature Ta, on the basis of a detection signal from the temperature sensor 180, and maintains the heater at this late preheating temperature Tb (second stage of the preheating mode).

Then, when the user sucks on the mouthpiece 104, the user's sucking action is sensed by the sucking sensing sensor 176 and a sensing signal is supplied to the control unit 168. Upon receiving the sensing signal, the control unit 168 quickly raises the heater 116 from the late preheating temperature Tb to an atomizing heating temperature Tc (220° C., for example), on the basis of a detection signal from the temperature sensor 180 (atomizing heating mode). The atomizing heating temperature Tc is a temperature of the heater 116 enough to atomize the solution L, namely turn it into an aerosol.

Thus, when the user does sucking action, the solution L is transferred from the distributing position A toward the heater 116, simultaneously with which, the heater 116 is raised to the atomizing heating temperature Tc. Consequently, all the solution that has entered the heater 116 is atomized, namely turns into an aerosol, under heat from the heater 116, and the aerosol formed is drawn into the user's mouth through the mouthpiece 104 together with the air flow.

It is to be noted that when the heater 116 reaches the atomizing heating temperature Tc, the control unit 168 stops supply of power to the heater 116. After this, when a detection signal from the temperature sensor 180 indicates that the heater 116 has fallen to the early preheating temperature Ta, the control unit 168 resumes supply of power to the heater 116 to maintain the heater 116 at the early preheating temperature Ta until the liquid supply switch 174 is put in the "ON" position next time (first stage of the preheating mode). The control unit 168 repeats the above-described temperature control.

Figure 9:
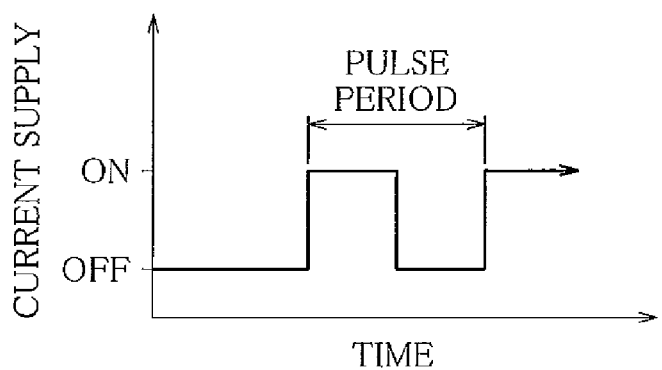

The above mentioned temperature control of the heater 116 is carried out by pulse-width modulation. As shown in FIG. 9, in the pulse-width modulation, duty cycle, namely the ratio of pulse "ON" time in which current is supplied to the heater 116 to pulse period is modulated. Specifically, the duty ratio D0 for the period from the time that the power switch 172 is put in the "ON" position until the heater 116 is raised to the early preheating temperature Ta is determined to be a maximum allowable for the electrical cell 162. The duty ratios D1, D2 for maintaining the heater 116 at the early and late preheating temperatures Ta, Tb, respectively, are each determined to be a minimum required for that. Further, the duty ratio D3 for raising the heater 116 from the late preheating temperature Tb to the atomizing heating temperature Tc is determined to be a maximum that does not cause a change in composition of the solution L. Such maximum value depends on the composition of the solution L.

The duty ratio D4 for raising the heater 116 from the early preheating temperature Ta to the late preheating temperature Tb may be determined to be equal to the duty ratio D3, for example.

As already clear from the above description, the heater 116 is raised to the late preheating temperature Tb before the user does sucking action. This reduces considerably the period of time between the user's starting sucking action and the heater 116 reaching the atomizing heating temperature Tc, and therefore allows the solution L to form an aerosol in the air drawn by user simultaneously with the user's sucking action, thereby preventing the user from feeling uncomfortable due to a time lag before generation of the aerosol.

All the solution L delivered to the distributing position A in the generation passage 110 turns into the aerosol within the generation passage 110, specifically within the heater 116. Thus, the aerosol obtained from the solution L, together with the air drawn, is efficiently sucked by the user, from the generation passage 110 through the mouthpiece 104. Consequently, the aerosol delivery rate does not depend on the volume of air sucked by the user and therefore is stable.

On the other hand, while the user stays without sucking action, the heater 116 is maintained at the early preheating temperature Ta lower than the atomizing heating temperature Tc, and it is after the liquid supply switch 174 is put in the "ON" position that the heater 116 is raised from the early preheating temperature Ta to the late preheating temperature Tb. This reduces the consumption of the electrical cell 162, namely prolongs the life of the cell 162.

Figure 10:
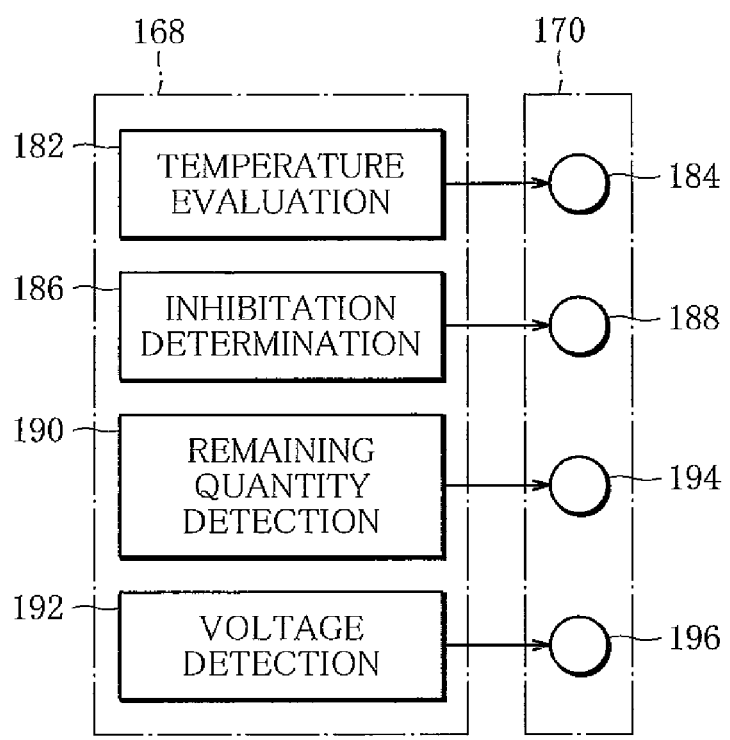

In the above description, it is assumed that the user starts sucking action with the heater 116 maintained at the late preheating temperature Tb (i.e., in the second stage of the preheating mode). In order to ensure that the user starts sucking action in such condition, the control unit 168 includes a temperature evaluation section 182 as shown in FIG. 10. The temperature evaluation section 182 determines whether or not the heater 116 has reached the late preheating temperature Tb, from a detection signal from the temperature sensor 180. If the result of determination is "true", the temperature evaluation section 182 causes the indicator 170 to indicate that the aspirator is "ready for sucking".

Specifically, in order to indicate that the aspirator is "ready for suction", the indicator 170 includes an indication lump 184, so that the user can start sucking action after confirming that the indication lump 184 is on. At the time that the user has started sucking action, the indication lump 184 is turned off.

When the aspirator is configured such that the syringe pump 130 is activated by the user putting the liquid supply switch 11 in the "ON" position as described above, it is desirable that the control unit 168 further include an inhabitation determination section 186. The inhabitation determination section 186 keeps the liquid supply switch 174 unenable until the user starts sucking action, i.e., a sensing signal is emitted from the sucking sensing sensor 176 after the syringe pump 130 is activated. Thus, even if the user puts, by mistake, the liquid supply switch 174 in the "ON" position in this period, the syringe pump 130 is not double-activated. This ensures that the amount of the solution L delivered to the distributing position A in the generation passage 110 is determined by a single action of the syringe pump 130.

The indicator 170 may include an indication lump 188 to indicate that activation of the syringe 170 is inhibited. In this case, the inhabitation determination section 186 turns on the indication lamp 188 simultaneously with inhibiting activation of the syringe 170 to tell the user that double activation of the syringe pump 130, thus double delivery of the solution L is inhibited.

When the user does sucking action and then the heater 116 reaches the atomizing temperature Tc, or supply of current to the heater 116 stops after that, activation of the syringe pump 130 is permitted and the indication lamp 188 is turned off.

The control unit 138 may further include a remaining quantity detection section 190 for detecting the amount of the solution L remaining in the syringe pump 130 and a voltage detection section 192 for detecting the voltage of the electrical cell 162, and the indicator 170 may include indication lamps 194, 196 corresponding to the remaining quantity detection section 190 and the voltage detection section 192, respectively.

As mentioned above, the amount of the solution L delivered from the syringe pump 130 each time the syringe pump 130 is activated is constant. Thus, the remaining quantity detection section 190 estimates the amount of the solution L remaining in the syringe pump 130 from the amount of the solution discharged from the syringe pump 130 in the aforementioned preprocessing, and at least either the number of times that the syringe pump 130 has been activated or the number of times that the sensing signal has been emitted from the sucking sensor 176. When the remaining quantity estimated decreases to a predetermined amount or below, the remaining quantity detection section 190 turns on the indication lamp 194 of the indicator 170 to tell the user that the remaining solution L is "scarce".

The voltage detection section 192 detects the output voltage of the electrical cell 162, and when the output voltage decreases to a predetermined value or below, turns on the indication lamp 196 of the indicator 170 to tell the user that "the remaining cell charge is scarce".

Indicating the states of the aspirator, specifically of the heater 116, syringe pump 130 and electrical cell 162 by the ON/OFF of the indication lamps 184, 188, 194 and 196 can help the user's appropriate use of the aspirator to suck an aerosol, and urge the preparation of a new syringe pump or electrical cell to replace the syringe pump 130 and or electrical cell 162.

As mentioned above, the heater 166 is removably set within the upper casing part 102a. This allows the user to remove the heater 116 and easily clean the generation passage 110 as well as the inside of the heater 116.

The indicator 170 may include a liquid crystal display in place of the indication lamps, for example. In this case, the above-mentioned various states are presented on the liquid crystal display.

Figure 11:
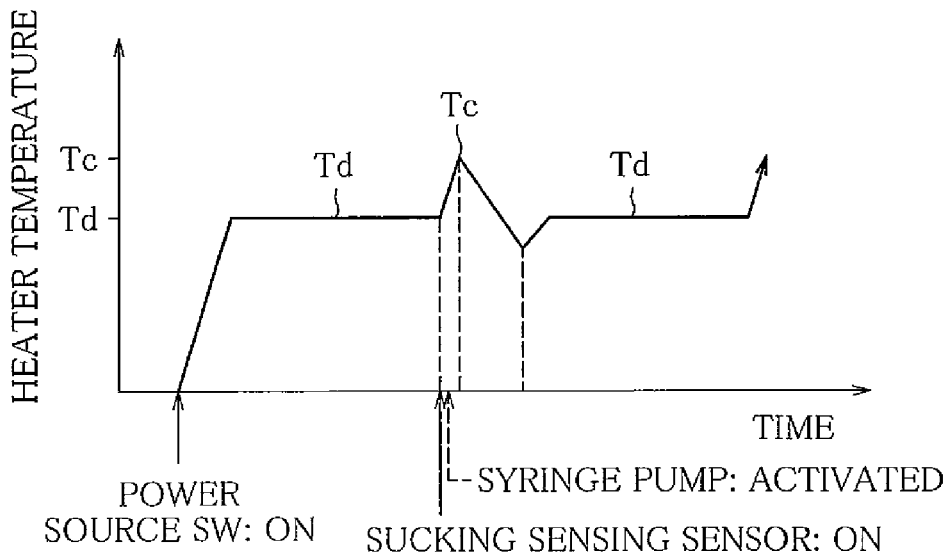
Figure 12:
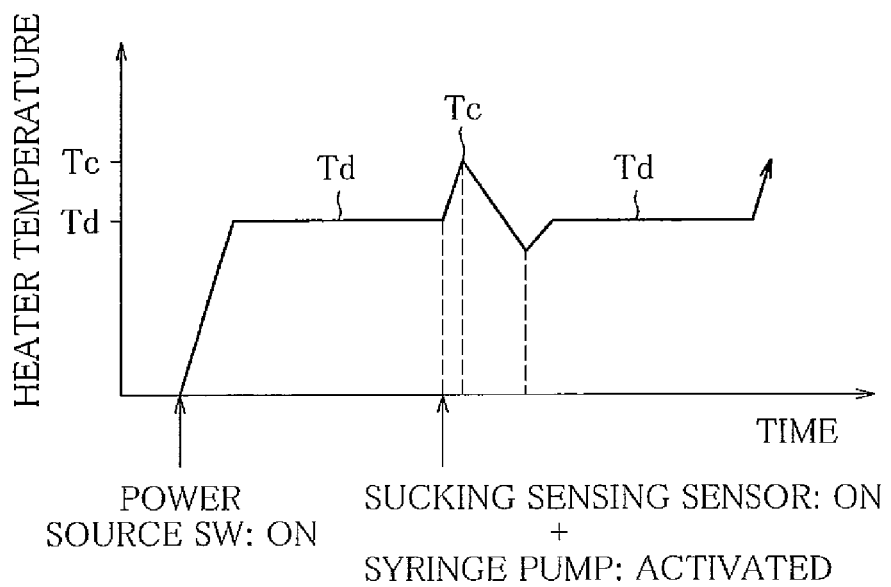

The liquid supply switch 174 is not indispensable. When the aspirator does not include the liquid supply switch 174, the control unit 168 controls the temperature of the heater 116 in a temperature control process, as shown in FIG. 11 or 12.

After the power switch 172 is put in the "ON" position, the control unit 168 raises the heater 116 to a preheating temperature Td lower than an atomizing heating temperature Tc and maintains it at this preheating temperature Td (preheating mode). Then the user starts sucking action, and when the sucking sensing sensor 176 emits a sensing signal, the control unit 168 raises the heater 116 to the atomizing heating temperature Tc (atomizing heating mode) and stops the supply of current to the heater 116.

Then, when the heater 116 falls to the preheating temperature Td or below, the control unit 168 resumes the supply of current to the heater 116 to raise the heater 116 back to the preheating temperature Td.

The control unit 168 may activate the syringe pump 130 to deliver a fixed amount of the solution L to the distributing position A in the generation passage 110, while the heater 116 is rising to the atomizing heating temperature Tc.

Specifically, as seen from the temperature control shown in FIG. 11, the control unit 168 activates the syringe pump 130 to deliver the solution L, while the heater 116 is rising from the preheating temperature Td to the atomizing temperature Tc. In this case, at the time that the solution L is delivered, air in the generation passage 110 has already been drawn toward the mouthpiece by the user's sucking on the mouthpiece 104, so that the solution L delivered to the distributing position A is immediately transferred into the heater 116, heated by the heater 116 and atomized, namely forms an aerosol with air sucked.

The solution L may be delivered while the heater 116 is maintained at the preheating temperature Td. Only the first delivery of the solution L may be carried out at the time that the power switch 172 is put in the "ON" position.

The preheating temperature Td may be equal to the aforementioned late preheating temperature Tb. However, considering that the user may repeat the sucking action continuously, the preheating temperature Td and the early preheating temperature Ta are so determined that the time taken for the heater 116 to reach the atomizing heating temperature Tc after the user's starting sucking action, thus, the time taken for generation of an aerosol may not cause the user to feel uncomfortable, and that preheating may not cause a change in composition of the solution L.

It may be adapted such that when the syringe pump 130 is activated to deliver the solution L to the distributing position A in the generation passage 110 and then the user puts the power switch 172 in the "OFF" position without performing sucking action, the control unit 168 performs a termination mode. The termination mode includes reverse operation of the syringe pump 130, thereby bringing the solution L back to the delivery portion or the pump chamber 140.

Such termination mode is performed also in the temperature control process shown in FIG. 8 using of the liquid supply switch 174.

In order to dispense with the aforementioned termination mode, the control unit 168 can adopt the temperature control process as shown in FIG. 12. In this temperature control process, the control unit 168 activates the syringe pump 130 upon receiving a sensing signal from the sucking sensing sensor 176. Since the delivery of the solution L is caused following the user's sucking action, the possibility that the solution L remains at the distributing position A in the generation passage 110 is eliminated.

In view of possible wrong operation of the power switch 172, it may be adapted such that the control unit 168 does not start or stop functioning unless the power switch stays in the "ON" or "OFF" position for a predetermined period of time. It is however desirable that the supply of current to the heater 116 be started at the same time as the power switch 172 is put in the "ON" position.

It may be adapted such that the control unit 168 makes ineffective the power switch 172 in the "ON" position, if the syringe pump 130 is not attached, or in other words, a sensing signal is not emitted from the cartridge sensing sensor 178.

Further, it may be adapted such that the control unit 168 has a function of storing usage history such as how many times the user has done suction action, how long power is supplied to the heater 116, how many times the syringe pump 130 has been replaced, etc.

Further, it may be adapted such that the aerosol aspirator includes a reading section to read information on the syringe pump 130 at the time that the syringe pump 130 is attached, if the syringe pump 130 has information such as the type and volume of solution in the form of a bar code or the like. In this case, it may be adapted such that the control unit 168 changes the temperature control process for the heater 116, depending on the solution type identified from the information read by the reading section 168.

An identity verification system based on fingerprint, an IC tag, an IC card or the like may be incorporated into the aerosol aspirator to reliably prevent unauthorized use of the aerosol aspirator. Further, the power source of the aerosol aspirator does not need to be accommodated within the casing.

Although the aerosol aspirator according to the embodiments described above all use a syringe pump to supply a solution, another type of fixed displacement pump, such as a gear pump, can be used.

The invention claimed is:

1. An aerosol aspirator comprising:
   a casing with a mouthpiece, said casing including an outside air inlet open to an outer surface thereof,
   a generation device disposed within said casing for generating an aerosol, said generation device including:
   a generation passage for generating an aerosol, the generation passage extending from the outside air inlet to the mouthpiece and having a distributing position and an evaporating position in a middle part thereof, the evaporating position being separated from the distributing position, downstream of the distribution position along the generation passage,
   a supply pump having a solution chamber holding a solution to be turned into an aerosol, for delivering the solution, in the form of a liquid, from the solution chamber to the distributing position, to close the generation passage with a fixed amount of the solution each time the supply pump is activated, the solution delivered to the distributing position being moved in said liquid form from the distributing position to the evaporating position as air in the generation passage is sucked by means of the mouthpiece, and
   a heater for evaporating the solution delivered to the evaporating position, the heater forming a part of the generation passage.

2. The aerosol aspirator according to claim 1, wherein the generation passage is a tubular passage.

3. The aerosol aspirator according to claim 1, wherein the supply pump is a syringe pump, and
   said generation device further includes a liquid passage connecting the syringe pump and the generation passage at the distributing position for closing the generation passage at the distributing position with the solution delivered from the syringe pump to the distributing position.

4. The aerosol aspirator according to claim 3, further comprising a switch for activating the heater prior to activating the syringe pump.

5. The aerosol aspirator according to claim 4, wherein said generation device further includes a push button manually operated to activate the syringe pump.

6. The aerosol aspirator according to claim 4, wherein said generation device further includes an actuator for activating the syringe pump, and a sucking sensing sensor for sensing sucking of air in the generation passage by means of the mouthpiece and activating the actuator.

7. The aerosol aspirator according to claim 1, wherein the generation device further includes a liquid passage connecting the distributing position of the generation passage and the supply pump, and the liquid passage is filled with the solution.

8. The aerosol aspirator according to claim 1, wherein the generation passage has a check valve inserted therein near the outside air inlet, and the check valve only allows the flow of outside air from the outside air inlet into the generation passage.

9. The aerosol aspirator according to claim 1, wherein the heater is tubular in shape.

10. The aerosol aspirator according to claim 1, wherein the distributing position and the evaporating position are separated from each other by a linear portion of the generation passage disposed therebetween.

11. A method for generating an aerosol from a solution using a user's sucking action which includes:
   a generation passage,
   a distribution position to which a solution to be turned into an aerosol is to be delivered, said distribution position disposed in the generation passage,
   an outside air inlet communicating with the generation passage at one end thereof and a mouth piece for generating the sucking action communicating with the generation passage at the other end thereof, and
   an evaporating position separately positioned in the generation passage between the distribution position and the mouth piece, said method comprising:
controlling the delivery of the solution to the distributing position and the evaporation of the solution at the evaporating position by drawing in air by the mouthpiece through the outside air inlet into the generation passage,
distributing a fixed amount of the solution to be converted into an aerosol to the distribution position of the generation passage to close the generation passage with said fixed amount of said solution between the outside air inlet and the evaporating position,
moving said fixed amount of solution, as a liquid mass, from the distributing position to the evaporating position, as air in the generation passage is drawn in by said mouthpiece, and
heating the liquid mass of solution in the evaporating position to form said aerosol.

* * * * *